United States Patent [19]

Makiej, Jr.

[11] Patent Number: 4,793,493
[45] Date of Patent: Dec. 27, 1988

[54] MULTIDOSE CAPSULES

[76] Inventor: Walter J. Makiej, Jr., 93 River Rd., Lowell, Mass. 01852

[21] Appl. No.: 82,034

[22] Filed: Aug. 5, 1987

Related U.S. Application Data

[62] Division of Ser. No. 908,823, Sep. 18, 1986.

[51] Int. Cl.$^4$ .............................................. B65D 85/42
[52] U.S. Cl. ................................... 206/538; 206/528; 206/531; 206/602; 424/467
[58] Field of Search ............... 206/219, 222, 528, 530, 206/532, 538, 539, 602; 220/4 D, 20, 22; 424/464, 467, 468

[56] References Cited

U.S. PATENT DOCUMENTS

| 462,990 | 11/1891 | Oppenheimer | 206/538 |
| 1,867,494 | 7/1932 | Buchner | 206/38 R |
| 2,334,600 | 11/1943 | Boysen | 206/532 |
| 2,534,229 | 12/1950 | Carhart et al. | 206/219 |
| 2,594,093 | 4/1952 | Thompson | 206/528 |
| 2,640,623 | 6/1953 | Ryder | 206/602 |
| 2,726,004 | 12/1955 | McLeod | 220/4.0 |
| 2,753,868 | 7/1956 | Seemar | 206/222 |
| 2,773,591 | 12/1956 | Jensen | 206/222 |
| 2,815,755 | 12/1957 | Anastor | 206/222 |
| 3,072,528 | 1/1963 | Kludas et al. | 206/538 |
| 3,451,540 | 6/1969 | Kulischenko | 206/222 |
| 3,927,737 | 12/1975 | Ernst et al. | 206/219 |
| 4,113,097 | 9/1978 | Finn | 206/528 |
| 4,215,104 | 7/1980 | Ullman et al. | 424/467 |
| 4,258,027 | 3/1981 | Ullman et al. | 424/467 |

FOREIGN PATENT DOCUMENTS

| 1131500 | 2/1957 | France | 206/219 |
| 1418020 | 12/1975 | United Kingdom | 206/602 |

Primary Examiner—David T. Fidei
Attorney, Agent, or Firm—Gaston & Snow

[57] ABSTRACT

The present invention is a multidose capsule including a tube having a first end and a second end and a dividing wall, supported by the tube, which separates the tube into first and second chambers. First and second removably supportable caps are slidable along each tube end to the extent sufficient to securely seal the chamber thereunder. In alternative embodiments both the dividing wall and the capsule periphery with respect thereto are frangible such that the capsule may be broken in two under an applied stress.

11 Claims, 3 Drawing Sheets

MULTIDOSE CAPSULES

This is a divisional of co-pending application Ser. No. 908,823 filed on Sept. 18, 1986.

FIELD OF ART

The present invention relates to medicinal capsules and, more particularly, relates to medicinal capsules for use in the titration of individualized drugs.

BACKGROUND OF THE ART

It is well known in the art that the dose required of certain drugs to achieve and maintain therapeutic and safe levels varies significantly from patient to patient. Because overdosing of such drugs can cause a myriad of severe side effects including nausea, vomiting, convulsions, ventricular arrhythmias, seizures and cardiorespiratory arrest, the maximum effective dose to be administered is ordinarily determined on an individualized basis. Theophylline, a drug used primarily as a bronchodilator, is typical of such individualized medications.

The present method for individualizing theophylline is by titration. During titration, the patient is given an initial dose of theophylline which, dependent upon serum theophylline measurement, is adjusted either upwardly or downwardly. Subsequent doses of theophylline are then accordingly increased or decreased until the maximum therapeutic dose is achieved. Unfortunately, each adjustment of the dose level during the titration cycle requires the patient to purchase a separate and distinct potency capsule since conventional capsules can only deliver a single predetermined theophylline dose. The cost for titrating theophylline in conventional capsule form can therefore become prohibitive, especially considering the fact that capsules of theophylline are ordinarily sold only in large quantities having a uniform potency.

An additional problem with the conventional capsules used to titrate theophylline is that oral administration of the drug by sprinkling fails to deliver the entire dose carried by the capsule. Regardless of the capsule orientation, removal of either end of the conventional capsule results in a significant quantity of the drug medium escaping over the edges of the capsule housing. Consequently, it is difficult to ascertain the exact dosage which is ultimately administered to the patient. Moreover, a patient may be tempted to administer a second dose of theophylline to compensate for the inadequate delivery of the first dose. Sprinkling theophylline or other individualized drugs from conventional capsules therefore poses a serious health risk to the patient, especially considering the severe side effects associated with overdose of such medications.

SUMMARY OF THE INVENTION

The present invention is a capsule for carrying multiple or graduating doses of medicinal particles, beads or liquids. In one important embodiment of the invention, the capsule includes a hard gelatin tube having a first end and a second end and a dividing wall, supported by the tube, which divides the tube into first and second chambers. A predetermined dose of the desired drug, in powder, bead or liquid form, is retainable in each of the first and second chambers. First and second removably supportable caps are then slidably mounted upon, and along, each tube end to seal each of the chambers, thereby preventing the medicinal contents from escaping. The drug contained within the capsule is orally administered by swallowing the capsule whole or by instead sliding the removably supportable caps from the tube and sprinkling the medicine contained therein onto a food carrier, through a nasal gastric tube or directly into the patient's mouth. Grasping means are preferably provided on either the tube or the removably supportable caps' periphery to facilitate removal of the caps from the tube thereunder when sprinkling is desired.

In another important embodiment of the invention, the capsule includes a hard gelatin tube having a first end and a second end and a frangible dividing wall, supported by the tube, which divides the tube into first and second chambers. The frangible dividing wall preferably includes a plurality of perforations extending through its cross section which facilitate rupturing of the dividing wall under an applied stress. Snapping of the tube in an axial direction causes the frangible dividing wall to fracture, thereby separating the multidose capsule into first and second capsule remnants as defined by the first and second chambers, respectively. The patient can administer the drug by either removing the caps from the capsule remnants and sprinkling or by leaving the caps on the remnants and ingesting the remnants whole. Grasping means are again provided to facilitate removal of the cap when sprinkling of the therapeutic drug is desired.

Accordingly, it is a primary object of the present invention to provide a capsule for carrying multiple or varying doses of medication.

It is another object of the present invention to provide a capsule which can be administered orally by either swallowing the capsule or sprinkling the medicinal medium contained within the capsule.

It is another object of the present invention to provide a capsule which is easily administrable to either geriatric, pediatric, tube fed patients or other individuals who have difficulty swallowing capsules whole.

It is another object of the present invention to provide a capsule which facilitates titration to the appropriate level without requiring the use of additional capsules having either increased or decreased dosage levels.

It is a still further object of the present invention to provide an inexpensive capsule that can be easily separated by the patient into varying predetermined doses.

BRIEF DESCRIPTION OF THE DRAWINGS

These and other details of the invention will be described in connection with the accompanying drawing in which.

DESCRIPTION OF THE PREFERRED EMBODIMENT

Figure 1:
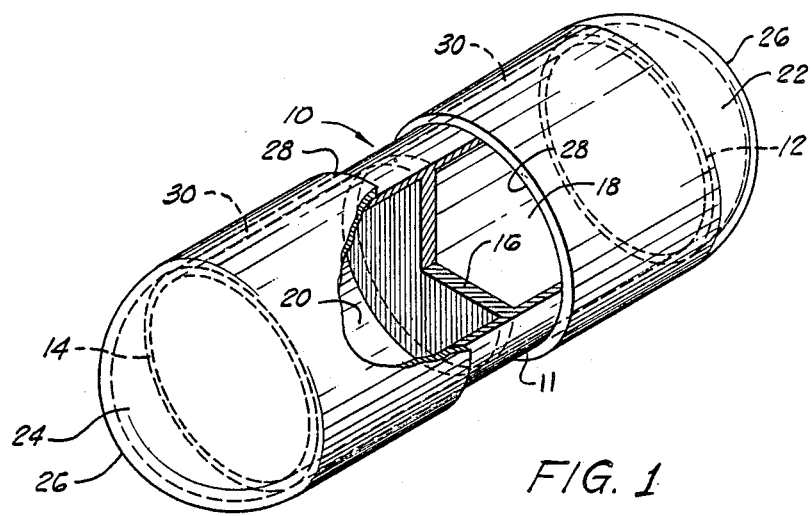
FIG. 1 is a perspective view, partly in section, showing the capsule according to the preferred embodiment of the invention.

The present invention is a capsule 10 for carrying multiple or graduating doses of a desired drug in either liquid, solid or particle form. In the preferred embodiment, the capsule includes a tube 11 having a first end 12 and a second end 14 and a dividing wall 16 that is supported by the tube 11. Dividing wall 16 separates the tube 11 into a first chamber 18 and a second chamber 20 which, preferably, are volumetric equivalents. The first chamber 18 is filled with the desired drug in either powder, particle or liquid form by any conventional means such as a Type 8 Standard Hard Capsule Filling Machine, distributed by Warner Lambert Company, or other capsule filling apparatus as is known to those skilled in the art. Subsequent to filling the first chamber 18 with the desired dose, removably supportable cap 22 is slidably mounted upon and along the first end 12 of tube 11. After the first chamber 18 has been sealed by the removably supportable cap 22, the second chamber 20 is accordingly filled with the appropriate dose level of the desired medication. The second removably supportable cap 24 is then slidably mounted upon and along the second end 14 of tube 11 to seal the second chamber 20. The resulting capsule 10 is therefore divided into two separate chambers, preferably containing equal volumetric amounts of the desired medication.

Tube 11, dividing wall 16 and removably supportable caps 22, 24 are each preferably fabricated from a hard gelatin material such as type A gelatin, type B gelatin or mixtures thereof. The gelatin may be either dyed or dye free dependent upon the ultimate application. Alternatively, the capsule components can be formed from other conventional materials as is known to those skilled in the art. The dividing wall 16 is preferably formed integral with the tube 11 in the manufacturing process. Alternatively, dividing wall 16 may constitute a separate element having dimensions congruous to, but slightly larger than, the cross section of the tube whereby the dividing wall is retainable in an annular channel in the interior periphery of the tube 11. Removably supportable caps 22, 24 are sealed at one end 26 and are opened at the other end 28. The sealed end 26 being rounded or constructed on a section of a sphere as in conventional capsules. Open end 28 is preferably flexible at least to the extent sufficient to facilitate mounting and sliding of the caps along the ends and extension 30 of the tube when sealing the chambers. In the preferred embodiment, the diameter of each of the removably supportable caps 22, 24 is slightly greater than the diameter of the associated tube end 12, 14 to enable mounting of the cap on the tube end thereunder. The resilient force of the open end 28 against the tube ends 12, 14 and tube extension 30 is sufficient to retain the caps 22, 24 on the tube 11 thereunder.

Multidose capsule 10 may be administered orally to the patient by either swallowing the capsule whole or by, instead, removing caps 22, 24 and sprinkling the drug beads contained therein into the mouth of the patient, onto a soft food carrier, through a nasal gastric tube or by other means known to those skilled in the art. The sprinkling capability of the multidose capsule 10 is especially beneficial for geriatric and pediatric patients who have great difficulty swallowing capsules as well as for nasal gastric fed patients who cannot swallow such capsules.

Figure 2:
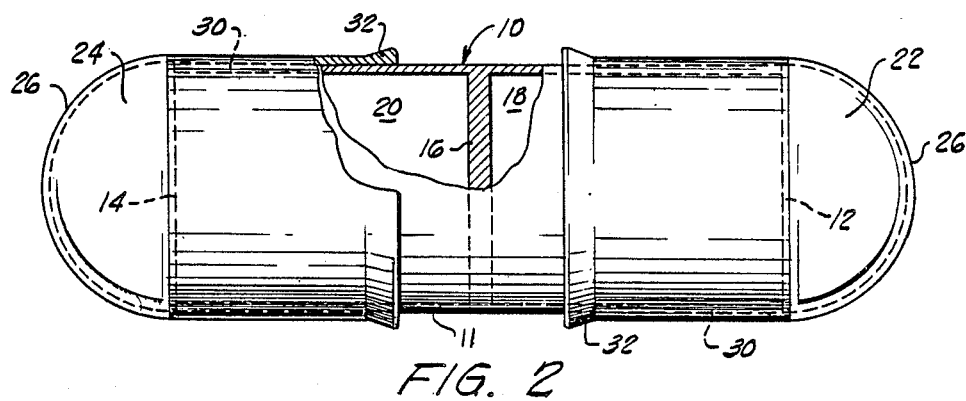
FIG. 2 is a perspective view, partly in section, of an alternative embodiment of the present invention illustrating the tapered annular flanges of the removably supportable caps.

Removably supportable caps 22, 24 are easily removed from the tube 11 by grasping sealed end 26 and gently sliding the caps 22, 24 in axial direction away from the tube 11. Capsule 10 is preferably held in a vertical position when the removably supportable cap is removed therefrom in order to prevent any of the beads, particles or liquid contained in the chamber from inadvertently escaping prior to administration. Removal of caps 22, 24 is facilitated by providing grasping means along the periphery of the caps. In the alternative embodiment shown in FIG. 2, the grasping means include annular flanges 32 which are integrally formed with the periphery of the first end 28 of each of teh first and second removably supportable caps 22, 24 and which extend radially outward from the cap surface. Annular flanges 32 are preferably cone-shaped, terminating near the middle of the cap and are smooth surfaced so that edges or rough spots do not inhibit swallowing of the capsule if sprinkling is undesired.

Figure 3:
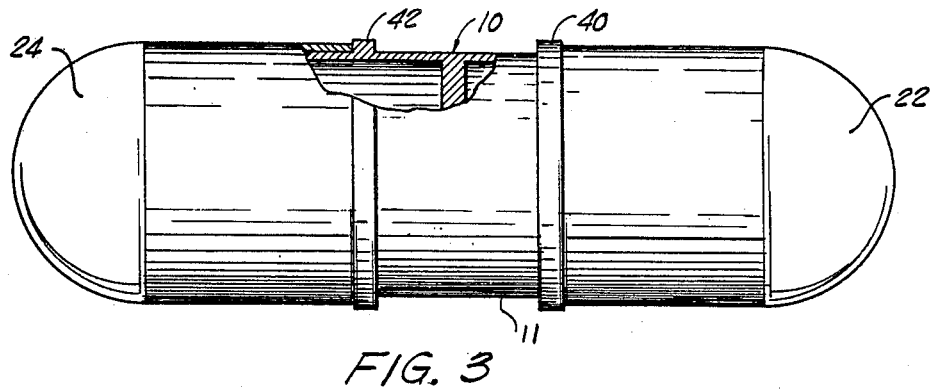
FIG. 3 is a perspective view of an alternative embodiment portraying the tube supported annular rings for facilitating removal of the removably supportable caps from the tube thereunder.

The grasping means for facilitating removal of the caps 22, 24 may, alternatively, be provided along the tube periphery as illustrated in FIG. 3. The grasping means preferably includes annular rings 40, 42 which are integrally formed with the tube periphery and which extend radially outwards from the tube surface. To seal the first and second chambers, open ends of the removably supportable caps are abutted against the annular rings 40, 42. By grasping either the first annular ring 40 or the second annular ring 42 and then sliding the associated removably supportable cap away therefrom, displacement of the cap from the tube is easily managed.

Figure 4A:
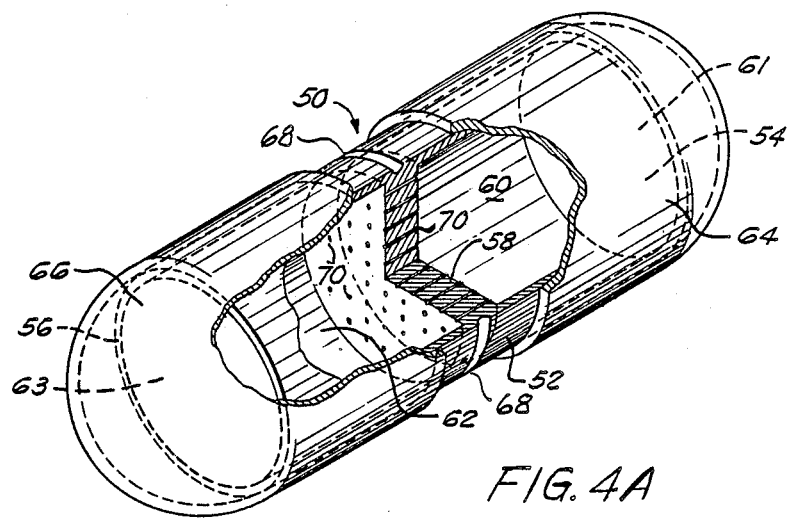
FIG. 4a is a perspective view, partly in section, showing a capsule having a frangible dividing wall according to an alternative embodiment of the present invention.

In an alternative embodiment shown in FIG. 4a, the capsule 50 includes a tube 52 having a first end 54 and a second end 56 and a frangible dividing wall 58 which is supported along the interior of the tube 52. Frangible dividing wall 58 divides the tube 52 interior into a first chamber 60 and a second chamber 62. First chamber 60 is filled through open end 61 with the appropriate level of the desired medication and then is sealed by first removably supportable cap 64. Second chamber 62 is subsequently filled through open end 63 with the appropriate drug dose and then sealed by second removably supportable cap 66.

Frangible dividing wall 58 is easily fracturable in half to allow the capsule 50 to be split into separate remnant units defined by the first and second chambers. Preferably, the frangible dividing wall contains a plurality of perforations or stress magnifiers 70 extending through its cross section or along its cross-sectional midplane which facilitate fracture of the dividing wall in half when stress is applied thereupon. The periphery 68 of tube 52 superposing the dividing wall is scored or notched with respect thereto so that the tube and dividing wall split along the same plane. Although the tube periphery relative to the dividing wall is preferably scored or notched, other means of increasing the frangibility of the tube at this locus may, alternatively, be utilized.

Figure 4B:
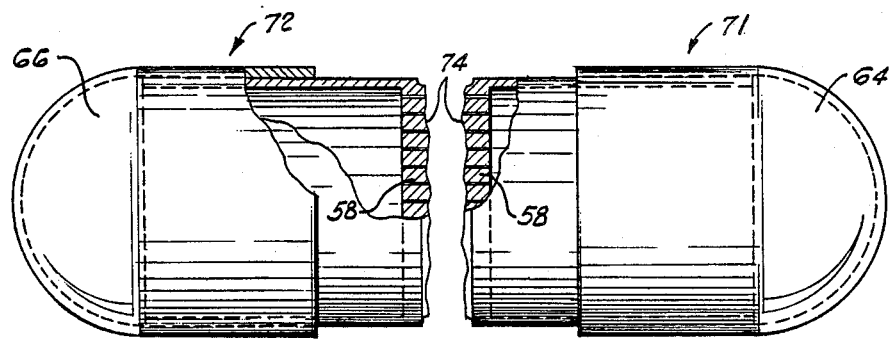
FIG. 4b is a perspective view, partly in section, illustrating the chamber remnants remaining after the frangible dividing wall of the capsule of FIG. 4a has been fractured.

Application of an appropriate stress along the dividing wall midplane, typically by snapping the tube between two points having the dividing wall as the midpoint, will result in separating the capsule into two separate single-dose capsule remnants 71, 72 as shown in FIG. 4b. The single-dose capsule remnants 71, 72 are sealed at one end by the removably supportable caps 64, 66 and at the other end by the remains 74 of the dividing wall 58. The single-dose capsules may be either swallowed in whole, or the medicinal contents may alternatively be received by sprinkling.

In an alternative embodiment, fracturing of the dividing wall in half is optimized by forming the dividing wall from a material which is inherently more frangible than the material from which the tube is fabricated. The inherently more frangible dividing wall preferably contains, in addition, fatigue points, such as blow holes or checks, which reduce the amount of force required to fracture the dividing wall. Bending the opposite ends of the tube therefore results in the dividing wall fracturing along its midplane. The tube periphery superposing the frangible dividing wall midplane is scored or notched to ensure a clean break of both the tube and frangible dividing wall when the breaking stress is applied. After the dividing wall and superposing tube periphery fracture, the multidose capsule separates into two single-dose capsules which are sealed at one end by removably supportable caps and at the other end by the remains of the dividing wall. The single dose capsules may now be orally administered to the patient by either swallowing the capsule whole or instead by sprinkling.

Figure 5:
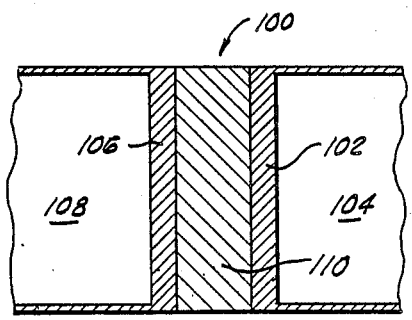
FIG. 5 is a sectional view showing a capsule including a three-section dividing wall according to an alternative embodiment of the invention.

Another alternative embodiment of the dividing wall is shown in FIG. 5. Dividing wall 100 consists of three sections: first section 102 which communicates with first chamber 104; second section 106 which communicates with second chamber 108; and third section 110 which is disposed between first section 102 and second section 106. First section 102 and second section 106 are made from the same material as the hard gelatin tube. Third section 110, however, is formed from a material which will fracture at a lesser stress than the hard gelatin material. Hence, under an applied stress, third section 110 will fracture before either of first section 102 or second section 106. The resulting single-dose capsule remnants are then sealed by the removably supportable caps at one end and by either the first section 102 or the second section 106 at the opposite end.

Figure 6:
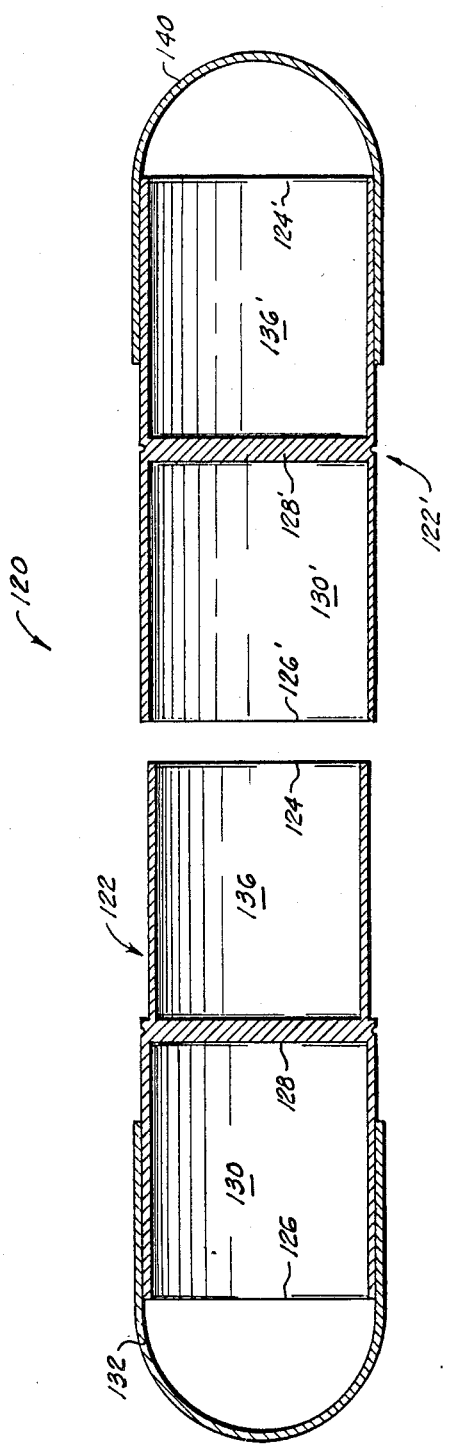
FIG. 6 is a perspective view, partly in section, illustrating a capsule according to an alternative embodiment of the present invention, having a first tube end which is receivable within a second tube end of an identically dimensioned tube.

The number of doses provided by the multidose capsule is further enhanced by administration of the capsule 120 shown in FIG. 6. Multidose capsule 120 includes tube 122 having a first end 124 and a second end 126 and a dividing wall 128, preferably frangible, which is supported by the tube. The diameter of the tube from the first end 124 to the dividing wall 128 is less than the diameter of the tube from the dividing wall 128 to the second end 126. As a consequence of these dimensions, first end 124 is receivable within the second end 126' of identically dimensioned tube 122'. Filling of the multidose capsule is accomplished by introducing the appropriate amount of the desired drug into second chamber 130 and then slidably mounting removably supportable cap 132 along the second end 126 until it is sufficiently supported by the tube 122 thereunder. First chamber 136 is then filled with the requisite level of medicine and then inserted into second end 126' of identically dimensioned tube 122'. Dividing wall 128 and dividing wall 128' seal the ends of the first chamber 136 retaining the therapeutic drug therein. First chamber 136' is subsequently filled with the desired dose of drug beads, particles or liquid and then is sealed by sliding removably supportable cap 140 along the first end 124' of the identically dimensioned tube 122'. The multidose capsule 120 produced by combining tube 122 with identically dimensioned tube 122' is capable of delivering three rather than two doses of the desired medication. Of course, additional identically dimensioned tubes could be joined to the existing multidose capsule whereby an almost limitless dose capability is deliverable by the present invention.

In the preferred embodiment, the first and second chambers of the multidose capsule are volumetric equivalents. Hence, the dose of medicinal particles, beads or liquid deliverable from each chamber is, equivalent. By administration of the drug contained in only one of the chambers, a single predetermined dose of medication may be delivered. Conversely, sprinkling or swallowing the contents of both chambers will result in a double dose of medication being administered. A triple dose of medication may be obtained by administering both chambers of one multidose capsule and one chamber of a second multidose capsule of equivalent dose capability. Additional multiple doses of medication are thereby provided by administration of further multidose capsule chambers. Varying the volume of the first and second chambers so that they are not equivalent further optimizes the spectrum of doses which can be delivered.

In the preferred embodiment, the deliverable dose of each chamber is 50 milligrams (mg) of medication. Of course, in alternative embodiments, varying chamber sizes, including those capable of delivering 25 mg, 60 mg, 75 mg, etc., of beads, particles or liquid may be utilized. Moreover, the dose provided by the first and second chambers need not be equivalent. Hence the first chamber may contain 75 mg of drug while the second chamber may contain only 25 mg of medication. Such a multidose capsule is therefore capable of delivering graduating doses of either 25 mg, 75 mg or 100 mg of the desired medication.

The multidose capsule, by providing graduating doses of medication in a single capsule, is particularly attractive for use in the oral administration of theophylline and other individualized drugs which require titration by the patient before the appropriate level of medication can be determined. In a typical titration cycle for theophylline, a multidose capsule having a first chamber containing 25 mg of drug and a second chamber containing 75 mg of medication is utilized for delivering the initial dose of 100 mg. The multidose capsule is administered by having the patient swallow the capsule whole or by sprinkling the drug contained in each chamber onto a food carrier which is then ingested by the patient. If the drug is not tolerated at this dose level, the next scheduled theophylline administration will consist of a decreased dose, preferably by 25%. This is easily accomplished with the multidose capsule by either breaking the capsule along the dividing wall and having the patient swallow the chamber remnant containing 75 mg of theophylline or by simply removing the removably supportable cap enclosing the 75 mg chamber and orally administering the theophylline by known sprinkling techniques. Conversely, if the initial dose of theophylline is too low, the subsequent dose administered to the patient will be increased. The increased dose, ordinarily 25%, may again be administered by either breaking off a 25 mg chamber from a multidose capsule and having the patient swallow the 25 mg remnant along with an unbroken 100 mg multidose capsule or by sprinkling the contents of the multidose capsule onto a food carrier along with the contents of a 25 mg chamber from an additional capsule. Further adjustments to the theophylline dose level until the maximum acceptable dose is reached are administered accordingly.

It is understood that the preceding description is given merely by way of illustration and not in limitation of the invention and that various modifications may be made thereto without departing from the spirit of the invention as claimed.

I claim:

1. An ingestable hard gelatin capsule for holding medication to be ingested which comprises:
   a longitudinally extending tube having a first end and a second end;
   at least one dividing wall intermediate said first and second ends and extending in a cross-sectional plane through said longitudinally extending tube which separates said longitudinally extending tube into a first and second chamber, said at least one dividing wall having frangible means for severing said at least one dividing wall along a plane perpendicular to said longitudinally extending tube; and
   first and second removably supportable caps wherein each of said first and second removably supportable caps has a first end which is open and a second end which is sealed such that said open end of said first removably supportable cap is slidable along and mountable upon said first end of said longitudinally extending tube and said open end of said second removably supportable cap is slidable along and mountable upon said second end of said longitudinally extending tube to an extent sufficient to support each of said first and second removably supportable caps on said longitudinally extending tube thereunder.

2. The invention as recited in claim 1 wherein said frangible means further includes a plurality of stress magnifiers extending through said plane of said at least one dividing wall perpendicular to said longitudinally extending tube.

3. The invention as recited in claim 1 wherein said frangible means is fabricated from a first material which will fracture at a lesser stress than a second material from which said longitudinally extending tube is fabricated.

4. The invention as recited in claim 3 wherein said frangible means fabricated from a first material further includes fatigue points extending through said plane of said at least one dividing wall perpendicular to said logitudinally extending tube.

5. The invention as recited in claim 1 wherein the periphery of said longitudinally extending tube is scored with respect to said at least one dividing wall.

6. The invention as recited in claim 1 wherein the periphery of said longitudinally extending tube is notched with respect to said at least one dividing wall.

7. The invention as recited in claim 1 wherein said at least one dividing wall includes three sections, a first section which is disposed relative to said first chamber, a third section which is disposed relative to said second chamber and a second section interposed between said first and third sections, said second section including said frangible means and being fracturable at a lesser stress than said first and third sections of said at least one dividing wall.

8. The invention as recited in claim 7 wherein said second section further includes a plurality of stress magnifiers extending through said plain perpendicular to said longitudinally extending tube.

9. The invention as recited in claim 7 wherein the periphery of said longitudinally extending tube is scored with respect to said second section of said at least one dividing wall.

10. The invention as recited in claim 1 wherein said first and said second removably supportable caps each further include grasping means supported along the cap periphery for facilitating removal of said first and said second removably supportable caps from said longitudinally extending tube thereunder.

11. The invention as recited in claim 10 wherein said grasping means includes an annular flange integrally formed with the periphery of said first end of each of said first and second removably supportable caps that extends radially outwards therefrom.

* * * * *